United States Patent
Jiang et al.

(10) Patent No.: US 7,407,566 B2
(45) Date of Patent: Aug. 5, 2008

(54) SYSTEM AND METHOD FOR SENSING USING DIAMOND BASED MICROELECTRODES

(75) Inventors: Li Jiang, Cambridge (GB); Timothy Gareth John Jones, Cottenham (GB); Clive Edward Hall, Nijmegen (NL)

(73) Assignee: Schlumberger Technology Corporation, Ridgefield, CT (US)

( * ) Notice: Subject to any disclaimer, the term of this patent is extended or adjusted under 35 U.S.C. 154(b) by 781 days.

(21) Appl. No.: 10/638,610

(22) Filed: Aug. 11, 2003

(65) Prior Publication Data

US 2005/0029125 A1 Feb. 10, 2005

(30) Foreign Application Priority Data

Aug. 4, 2003 (GB) .................................. 0318135.1

(51) Int. Cl.
*G01N 27/403* (2006.01)
(52) U.S. Cl. .................... 204/400; 204/409; 204/433
(58) Field of Classification Search ................ 204/412, 204/406, 400, 408, 409, 410, 411, 415, 416, 204/421, 422, 433, 434, 280; 205/775, 782.5, 205/786.5, 787.5, 793, 794.5
See application file for complete search history.

(56) References Cited

U.S. PATENT DOCUMENTS

| | | | |
|---|---|---|---|
| 3,780,575 A | | 12/1973 | Urbanosky |
| 3,859,851 A | | 1/1975 | Urbanosky |
| 4,049,503 A | * | 9/1977 | Becker et al. ............. 205/779.5 |
| 4,062,750 A | * | 12/1977 | Butler ......................... 257/253 |
| 4,721,601 A | * | 1/1988 | Wrighton et al. .......... 422/82.03 |
| 4,994,671 A | | 2/1991 | Safinya |
| 5,071,527 A | * | 12/1991 | Kauffman .................... 205/786 |
| 5,296,125 A | * | 3/1994 | Glass et al. .................. 430/311 |
| 5,378,343 A | * | 1/1995 | Kounaves et al. ........... 204/413 |
| 5,512,489 A | * | 4/1996 | Girault et al. ............ 205/777.5 |

(Continued)

FOREIGN PATENT DOCUMENTS

EP 1 156 136 A 11/2001

(Continued)

OTHER PUBLICATIONS

Fujishima A.; Rao, Tata N.; Popa, E.; Sarada, B.V.; Yagi, I.; Tryk, D.A.; Electroanalysis of dopamine and NADH at conductive diamond electrodes; 1999; Journal of Electroanalytical Chemistry, vol. 473; pp. 179-185.*

(Continued)

*Primary Examiner*—Kaj K Olsen
(74) *Attorney, Agent, or Firm*—Steven Gahlings, Esq.; James McAleenan, Esq.; Jody Lynn DeStefanis, Esq.

(57) ABSTRACT

A method and system is disclosed for monitoring one or more characteristics associated with a fluid. An insulating layer comprising non-conducting diamond is positioned within a housing and has a surface exposed directly or indirectly to the fluid. A plurality of microelectrodes made of electrically conducting diamond each have a surface exposed directly or indirectly to the fluid. An electrical circuit in electrical communication with each of the microelectrodes is adapted to convert electrical signals from the microelectrodes into at least one signal associated with a characteristic being monitored. The sensing system is well suited to hydrocarbon wellbore related applications, but can also be used in other applications.

36 Claims, 7 Drawing Sheets

U.S. PATENT DOCUMENTS

| | | | |
|---|---|---|---|
| 5,656,827 | A | 8/1997 | Kang et al. |
| 6,740,216 | B2 * | 5/2004 | Diakonov et al. ............ 204/418 |
| 6,824,669 | B1 * | 11/2004 | Li et al. .................... 205/777.5 |
| 2003/0134426 | A1 | 7/2003 | Jiang et al. |
| 2005/0072672 | A1 * | 4/2005 | Hoom ......................... 204/416 |

FOREIGN PATENT DOCUMENTS

| | | |
|---|---|---|
| GB | 2 391 314 A | 2/2004 |
| JP | 05-018935 A | 1/1993 |
| WO | 01/88522 A2 | 11/2001 |

OTHER PUBLICATIONS

Wu, Jiali; Zhu, Jianzhong, Guoxiong; Chen, Nianyi; Fabrication and application of diamond film glucose biosensor based on microarray electrodes; 1996; Fenxi Huaxue; 24 (7); Abstract.*

Zhang et al, Materials Letters 18, 1994, pp. 318-319.*

Wu et al, Fenxi Huaxue, 1996, 24(7), pp. 768-772.*

Jeroschewski et al Galvanic sensor for determination of hydrogen sulfide Electroanalysis, vol. 6, No. 9, Sep. 1994, pp. 769-772.

Madore et al Detection of trace silver and copper at an array of boron-doped diamond microdisk electrodes Proceedings of the symposium on microfabricated systems and mems, vol. 2000-19, Oct. 2000, pp. 159-168.

Badry et al New wireline formation tester techniques and applications Trans. SPWLA 34th Ann. Logging Symp., Calgary, Jun. 1993, paper ZZ.

Cvacka et al Boron-doped diamond microelectrodes for use in capillary electrophoresis with electrochemical detection Analytical Chemistry, vol. 75, No. 11, 2003, pp. 2678-2687.

Downard Electrochemically assisted covalent modification of carbon electrodes Electroanalysis, vol. 12, No. 14, 2000, pp. 1085-1096.

Fletcher et al RAM™ electrodes—an introduction CSIRO Minerals Report, ISBN 0 642 20197 8, May 1995, pp. 1-18.

Kuo et al Electrochemical modification of boron-doped chemical vapor deposited diamond surfaces with covalently bonded monolayers Electrochemical and Solid-State Letters, vol. 2, No. 6, 1999, pp. 288-290.

McCreery Carbon electrodes: structural effects on electron transfer kinetics Electroanalytical chemistry (Allen J. Bard ed.), Marcel Dekker, New York, vol. 17, 1991, pp. 221-374.

McKenzie et al Adsorption and reactivity of hydrous iron oxide nanoparticles on boron-doped diamond Electrochemistry Communications, vol. 4, No. 10, 2002, Elsevier Science B.V., pp. 820-824.

Nagao et al Stability of field emission current from boron-doped diamond thin films terminated with hydrogen and oxygen Japanese Journal of Applied Physics, vol. 36, part 2, No. 9A/B, 1997, pp. L1250-L1253.

Ojani et al A cyclic voltammetric study of the aqueous electrochemistry of some anthraquinone derivatives on carbon paste electrode Iranian Journal of Chemistry and Chemical Engineering, vol. 20 No. 2, 2001, pp. 75-81.

Pitter et al Electron spectroscopy study of the silver-diamond(100)-H interface Applied Physics Letters, vol. 69, No. 26, 1996, pp. 4035-4037.

Schlumberger Pressure testing and sampling in cased wells CHDT Cased Hole Dynamics Tester, Schlumberger product brochure, Mar. 2002.

Shin et al Application of diamond microelectrodes for end-column electrochemical detection in capillary electrophoresis Analytical Chemistry, vol. 75, No. 3, 2003, pp. 530-534.

Soh et al CVD diamond anisotropic film as electrode for electrochemical sensing Sensors and Actuators, B 91, 2003, Elsevier Science B.V., pp. 39-45.

* cited by examiner

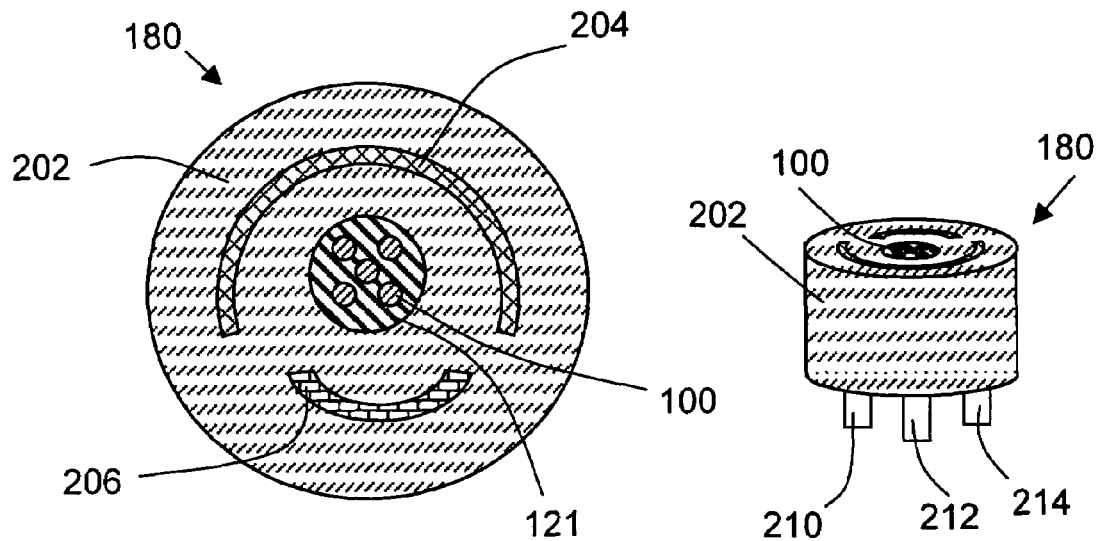
Figure 5a
Figure 5b
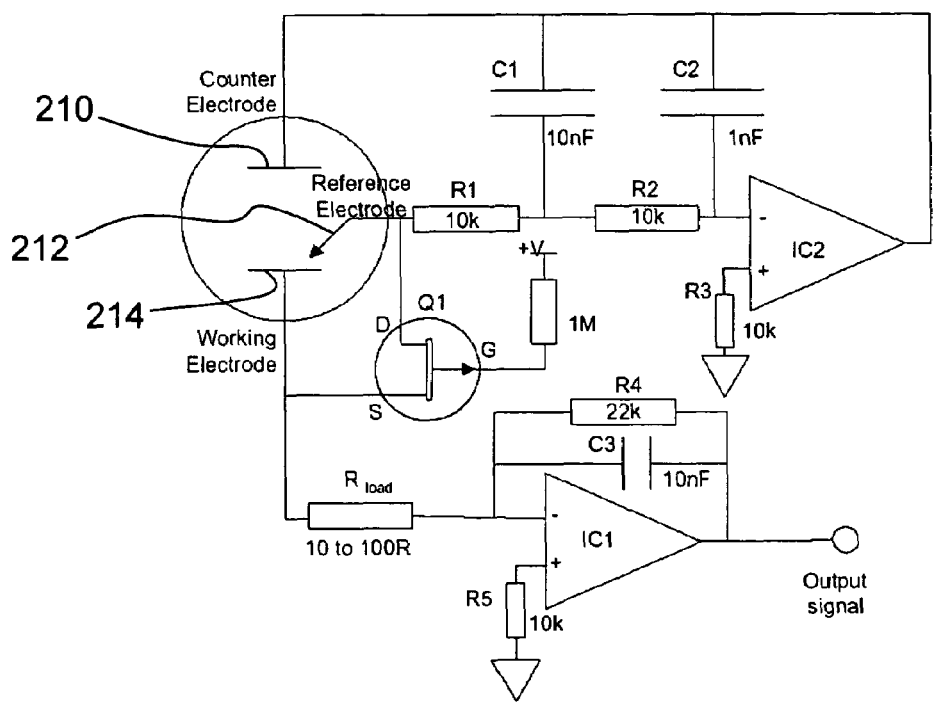
Figure 6

US 7,407,566 B2

SYSTEM AND METHOD FOR SENSING USING DIAMOND BASED MICROELECTRODES

FIELD OF THE INVENTION

The present invention relates to the field of sensors for monitoring characteristics of fluids. In particular, the invention relates to a system and method for monitoring chemical species, chemical properties and the like using diamond-based electrodes. Even more particularly, the invention preferably relates to such sensors used for fluid monitoring in relation to the development of hydrocarbon and water reservoirs.

BACKGROUND OF THE INVENTION

The use of carbon electrodes for electrochemical sensing is known. For example, see: Richard L. McCreery, "Carbon electrodes: structural effects on electron transfer kinetics", in "Electroanalytical Chemistry", Ed. Allen J. Bard, Volume 17, pp 221-374, 1991, Marcel Dekker, New York. In addition, it has been proposed to reduce the size of graphite electrodes as is described in: S. Fletcher and M. D. Horne, "RAM Electrodes—An Introduction", CSIRO Minerals, ISBN 0 642 20197, May 1995. However, we have found that carbon materials such as graphite tend to become quickly fouled when used in the harsh conditions of the oilfield. For example, under the pressures and temperatures in a hydrocarbon well, the chemicals present may absorb onto the surface of the graphite electrode.

Various configurations of diamond material have also been recently proposed as electrodes. See, Soh, Kang, Davidson, Wong, Wisitora-at, Swain and Cliffel, "CVD diamond anisotropic film as electrode for electrochemical sensing", Elsevier Science B.V., 2003; Cvacka, Quaisorova, Park, Show, Muck and Swain, "Boron-Doped Diamond Microelectrodes for Use in Capillary Electrophoresis with Electrochemical Detection", Analytical Chemistry, Vo. 75. No. 11, American Chemical Society, June 2003; and Shin, Sarada, Tryk, and Fujishima "Application of Diamond Microelectrodes for End-Column Electrochemical Detection in Capillary Electrophoresis", Analytical Chemistry, Vol. 75, No. 3., American Chemical Society, February 2003. The Soh et al. article discloses the use of a diamond based electrode which is about 0.2 sq. centimeters. We have found that the signal to noise ratio is often too low with this type of design. The Cvacka et al. article discloses depositing a thin film of boron doped diamond on electrochemically sharpened platinum wires. This design suffers from relatively low signal to noise ratio, and it is believed that the geometry would be relatively fragile in many applications. The Shin et al. article discloses single boron doped diamond electrode which will generally require a large amplification circuit and will not be robust enough for certain application, especially downhole.

SUMMARY OF THE INVENTION

According to the invention a sensor for monitoring one or more characteristics associated with a fluid is provided. The sensor preferably comprises a housing; an insulating layer comprising non-conducting diamond positioned within said housing and having a surface exposed directly or indirectly to the fluid; a plurality of microelectrodes each comprising electrically conducting diamond and having a surface exposed directly or indirectly to the fluid; and an electrical circuit in electrical communication with each of the microelectrodes adapted to convert electrical signals from the microelectrodes into at least one signal associated with a characteristic being monitored.

The size of the exposed surface of each microelectrode is preferably less than 8000 sq. microns, and even more preferably less than 2000 sq. microns. The sensor preferably includes at least seven microelectrodes, and even more preferably at least 19 microelectrodes. The microelectrodes are preferably arranged within the insulating layer such that the exposed surfaces of the microelectrodes form a regular pattern, even more preferably a hexagonal pattern. The distance between two adjacent microelectrodes is preferably at least five times, and even more preferably ten times, the diameter of a circle having an area equal to the area the exposed surface of each microelectrode. The insulating layer and the exposed surface each of the microelectrodes is preferably co-planar with the exposed surface of the insulating layer. For some applications, it is preferred to mount a gas permeable membrane between a main flow of fluid and the exposed surfaces of the insulating layer and the microelectrodes, wherein the sensor is adapted to sense characteristics associated with gas that is allowed to pass through the membrane. The thickness of the microelectrode layer is preferably more than 1 mm.

The characteristics of the fluid being monitored by the sensor can include chemical properties such as pH, the presence and/or concentration of a chemical species such as hydrogen sulphide, or a property of the fluid such as resistivity. The sensor is preferably incorporated into a wellbore sampling tool, a production logging tool, or a measurement-while-drilling subassembly. The sensor can also form part of a system to monitor fluids produced from or being pumped into wellbores.

The present invention is also embodied in a method for monitoring one or more characteristics associated with a fluid.

As used herein the term diamond refers to carbon with characteristic cubic crystalline structures (or crystal lattices). Diamond can be single-, poly- or nano-crystalline.

BRIEF DESCRIPTION OF THE DRAWINGS

FIGS. 5a and 5b show the placement of a diamond based microelectrode array in a housing, according to a preferred embodiment of the invention;

FIG. 6 is an electrical schematic diagram showing a preferred circuit layout for a sensor, according to the invention;

DETAILED DESCRIPTION OF THE INVENTION

Figure 1A:
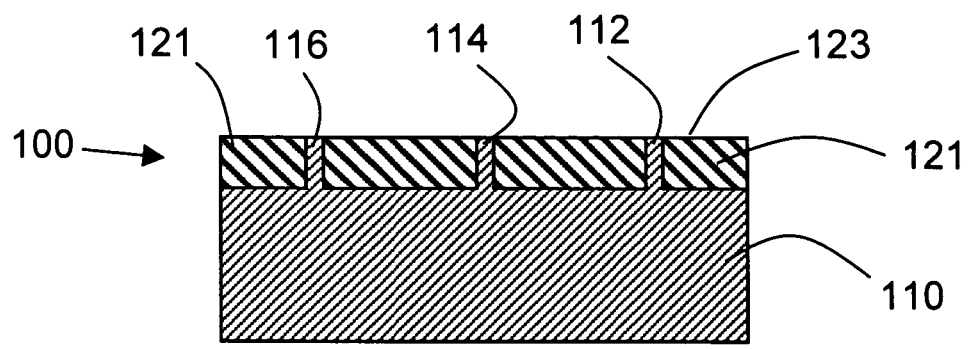
FIGS. 1a and 1b show a diamond-based microelectrode array according to a preferred embodiment of the invention.

The present invention is embodied in devices preferably based on diamond-based arrays of microelectrodes. Using diamond-based arrays of microelectrodes, redox active species can be detected and measured. Such diamond-based array sensors can advantageously be deployed in the oilfield environment where such redox active species measurement and detection are often critical to activities such as well-drilling, formation evaluation and production processes. According to the invention, a non-conductive substrate is provided which is composed of intrinsic diamond, and one or more conductive portions are provided composed preferably of boron-doped diamond. These devices combine the advantages of both macroelectrodes (such as measurable current scale) and microelectrodes (such as improved signal-to-noise ratio). Accordingly, the new sensors have significant potential for operations in harsh conditions such as the borehole environment.

The invention preferably makes use of diamond devices manufactured using high precision manufacturing techniques such as described in co-pending patent applications filed in the UK Patent Office on 4 Aug. 2003 by applicant Element Six Limited, and filed in the US Patent & Trademark Office on 11 Aug. 2003 to Clive Edward Hall et al., both entitled "Diamond Microelectrodes", which are incorporated herein by reference. According to preferred embodiments of the invention, a series of such devices are provided, where a non-conducting (preferably intrinsic) diamond surface containing multiple coplanar areas of conducting diamond. The areas of conducting diamond are preferably in electrical communication with each other and are separated on main surface of the non-conducting diamond.

Diamond-based sensors described herein have a number of advantages over conventional sensors, such as the following.

1. An all-diamond structure is well suited for application in extremely harsh environments such as that of a well-bore. In particular, diamond-based sensors are well suited for operation over an extended range of elevated temperatures and pressures. Thus, providing a relatively long service time which can include multiple usages.

2. The diamond-based sensors described herein provide significantly higher signal-to-noise ratio than conventional macroelectrodes.

3. The total current output is a sum of individual microelectrodes (i.e. there is no significant overlapping in the diffusion spheres of neighbouring electrodes), hence considerably larger current scale is provided that generally falls in the range of ready measurement without the need for complex electronic circuits.

4. The diamond-based sensors described herein provide significantly higher signal-to-(capacitively coupled) interference ratio than single microelectrode.

5. The diamond-based sensors described herein are relatively free from current leakage between individual conducting domains, which is important for epoxy-based microelectrode and its arrays.

6. The sensors described allow rapid attainment of the steady state in mass transport, and allow relatively fast potential scan (~100V/s) without distortion in the i-V characteristics.

7. The sensors described are useful in highly resistive and/or viscous media such as crude oil.

8. The use of diamond materials for electrodes advantageously provides a wide range of operation potentials for monitoring redox reactions.

Figure 1B:
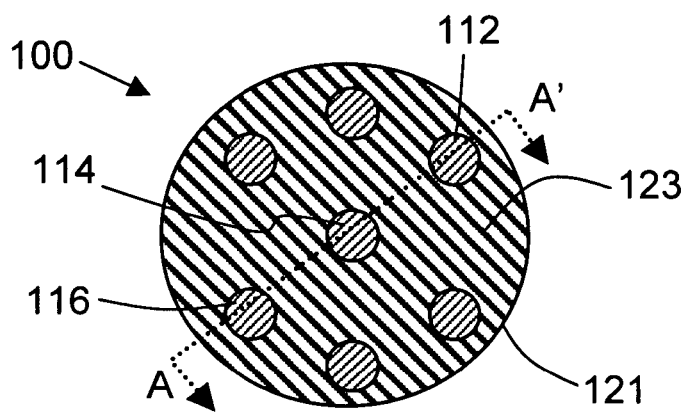

FIGS. 1a and 1b show a diamond-based microelectrode array according to a preferred embodiment of the invention. FIG. 1a is a cross-section of microelectrode array 100 along the line A-A' as shown in FIG. 1b which is a plan view of microelectrode array 100. Diamond layer 121 is non-conducting preferably intrinsic diamond and may be single crystal or polycrystalline in structure. Diamond layer 121 will typically be synthetic although natural diamond could also be used. Synthetic diamonds used in the present invention include high-pressure high-temperature (HPHT) diamond, as well as chemical vapour deposition (CVD) diamond. The upper surface 123 of diamond layer 121 will generally be smooth and preferably polished to a surface roughness of less than 100 nm Ra.

The upper surface area of conducting microelectrodes 112, 114 and 116 are coplanar with surface 123 of diamond layer 121. Microelectrodes 112, 114 and 116 are preferably boron (or S or P) doped diamond. Diamond microelectrodes 112, 114 and 116 are electrically connected to a lower portion 110 which is preferably non-conducting intrinsic diamond. The doping of microelectrodes 112, 114 and 116 is performed either during synthesis or subsequently via implantation. According to alternative embodiments of the invention, lower portion 110 is made of a non-diamond material such as graphite, which may be grown or implanted or metal which may be deposited using any known techniques (vapour deposition, sputter deposition, laser ablation, a diamond growth substrate that has not been removed, electroplating or implantation). The vertical length of the microelectrodes 112, 114 and 116, i.e. the distance from the exposed upper surface to the top of the lower portion 110, is preferably greater than 1 mm. It has been found that providing a length of 1 mm or greater improves the dynamic range of electric potential values for the sensing device.

FIG. 1b shows a plan view of a hexagonal coplanar arrangement of microelectrodes—note that the microelectrodes, including microelectrodes 112, 114 and 116 and the other microelectrodes are arranged in a hexagonal geometrical pattern in layer 121. The hexagonal arrangement shown is preferable because it allows for a relatively large spacing between microelectrodes for a given number of microelectrodes (in this case, seven) and a given surface area. In general it is preferable to maintain a certain spacing between microelectrodes so as to increase the volume from which diffusion will allow interaction with an electrode (the "diffusion sphere").

In general, it has been found that the distance between neighbouring microelectrodes should at least five and preferably about ten times larger than the diameter of the individual electrode surfaces. If the surface area of the microelectrodes are not circular, the general rule would be to space the microelectrodes apart more than five and preferably ten times the diameter of a circle having the same surface area the non-circular microelectrodes. Advantageously, it has been found that if the general design rule of ten times the diameter is followed, in many applications the diffusion spheres of the microelectrode areas do not overlap, but the number of microelectrodes is high enough for a given surface area such that the signal to noise ratio is significantly enhanced over conventional arrangements.

As used herein the term microelectrode refers to electrodes that have a relatively small surface area. It has been found that significant improvements in signal to noise ratio where each circular microelectrode has a diameter of 100 microns or less. Even better signal to noise ratios can be obtained with 50 micron diameters and even smaller diameters, such as 25 microns. If the microelectrodes are not circular, the exposed surface area of the non-circular microelectrodes should be less than 8000 sq. microns, and preferably less then 2000 sq. microns, and even more preferably less than 500 sq. microns. In general the lower limit of the electrode surface size will be largely due to limitations of the process technologies used.

Although seven microelectrodes are shown in FIG. 1b, other numbers can be used. In general, although a single microelectrode can work for some applications, two or more microelectrodes will provide greater sensitivities in particular applications. With greater numbers of microelectrodes, the signal strength will be greater, thereby placing less demand on the amplification circuitry required. In addition, due also to the redundancy of multiple microelectrodes, the design of multiple microelectrodes is more robust and well suited for applications such as the downhole environment. It has been found that providing from 7 to 19 microelectrodes allows for a reasonable signal strength and redundancy for many oilfield-related applications.

Figure 1C:
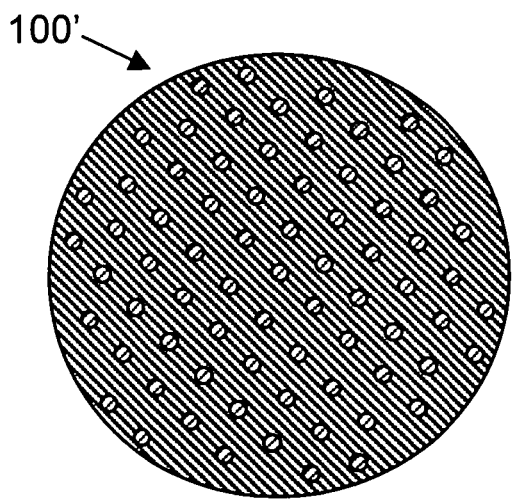
FIG. 1c shows a microelectrode array according to another embodiment of the invention.

FIG. 1c shows a microelectrode array according to another embodiment of the invention. Array 100' is shown with a hexagonal pattern of 73 microelectrodes. In general any number of microelectrodes can be used, and greater numbers of microelectrode areas should be provided when for applications requiring detection of very low concentrations of analytes. In addition, as used herein the term "array" refers to a plurality of elements not necessarily arranged in a regular pattern. For example, a non-regular distribution of microelectrode area can be provided, in some cases the spatial distribution of the microelectrode array can be random.

Figure 1D:
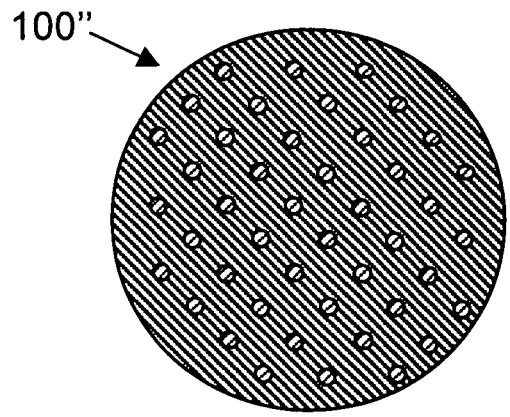
FIG. 1d shows a microelectrode array having a square pattern, according to another embodiment of the invention.

FIG. 1d shows an example of a microelectrode array 100" having a square pattern, according to another embodiment of the invention.

Figure 2:
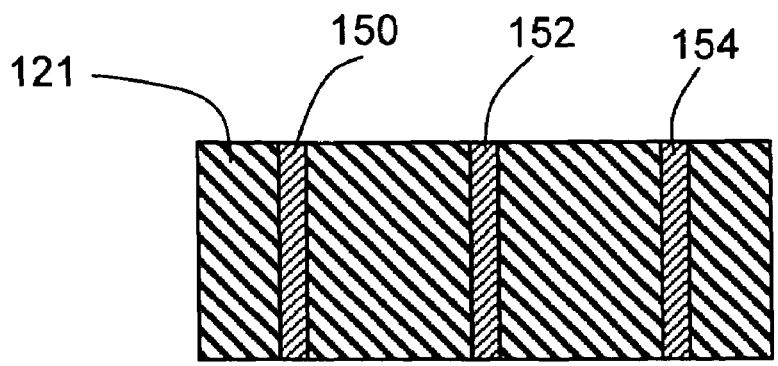
FIG. 2 show an arrangement of microelectrodes in a diamond layer according another embodiment of the invention.

FIG. 2 show an arrangement of microelectrodes in a diamond layer according to another embodiment of the invention. As in the embodiment described in FIGS. 1a and 1b, diamond layer 121 is preferably non-conducting intrinsic diamond and may be single crystal or polycrystalline in structure. Diamond layer 121 will typically be synthetic although natural diamond could also be used. Synthetic diamonds used in the present invention include high-pressure high-temperature (HPHT) diamond, as well as chemical vapour deposition (CVD) diamond. The upper surface 123 of diamond layer 121 will generally be smooth and preferably polished to a surface roughness of less than 100 nm Ra.

Microelectrodes 150, 152 and 154 are not electrically connected to a lower layer as in FIGS. 1a and 1b, rather they are individually addressable. Thus the microelectrodes may be used to sense different chemical properties or chemical species if they are each coated with different functional coatings as described herein below. For example, through different modifications as described below, microelectrodes 150 and 152 could be made to probe different target species. Electrodes 150, 152 and 154 are preferably made from boron doped diamond and arranged in a hexagonal layout, as described above, but could also be made by other doping techniques, or using other materials, or other geometrical arrangements as also described herein. Note that the surface of the microelectrodes are essentially coplanar with the surface of diamond layer 121.

Figure 3:
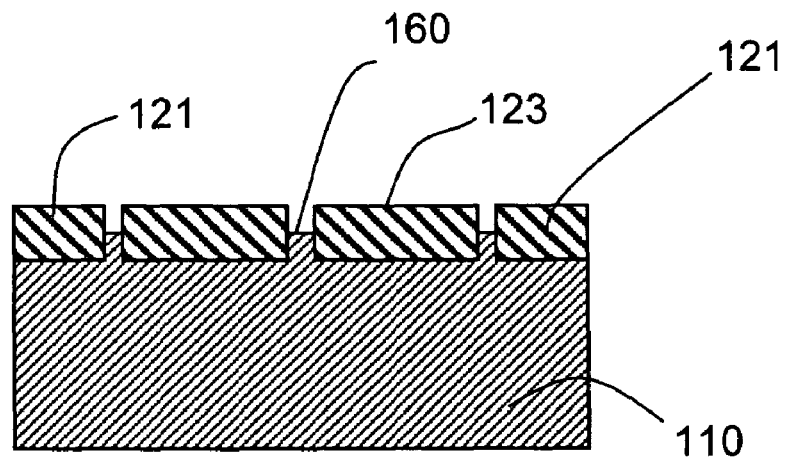
FIG. 3 shows an array of microelectrodes according to another embodiment of the invention.

FIG. 3 shows an array of microelectrodes according to another embodiment of the invention. In this embodiment the surfaces of the microelectrodes, for example microelectrode 160 are recessed below the surface 123 of diamond layer 121. Microelectrodes as shown in FIG. 3 have a reduced or more restricted diffusion sphere volume which may be desirable in some applications.

Figure 4:
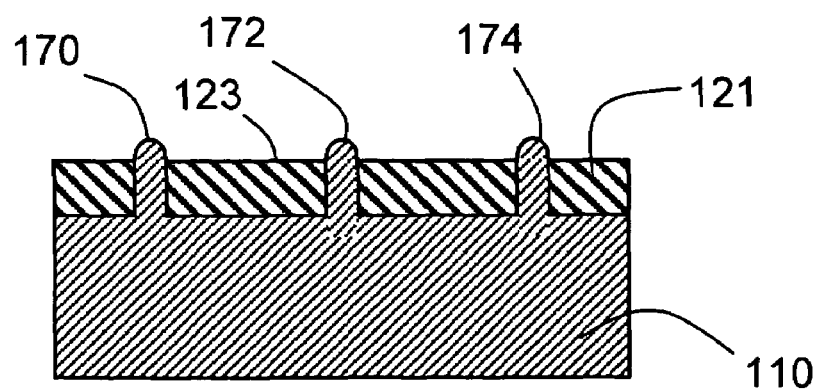
FIG. 4 shows an array of microelectrodes according to another embodiment of the invention.

FIG. 4 shows an array of microelectrodes according to another embodiment of the invention. In this embodiment the microelectrodes 170, 172 and 174 protrude above the surface 123 of diamond layer 121. In addition, the shape of the exposed microelectrodes is rounded to a spherical shape. Microelectrodes as shown in FIG. 4 have the advantage of enhancing the size of the diffusion sphere volume for each microelectrode which may be desirable in some applications. The materials and arrangements of the microelectrodes and the underlying layer 110 are preferably as described above with respect to FIGS. 1a and 1b.

The surface of the microelectrodes can be bare, i.e. unmodified, wherein the boron-doped diamond alone is the reacting surface. This may be suitable for example to sensing the presence of hydrogen sulphide. For an example of sensing hydrogen sulphide with a bare reaction surface see co-pending PCT patent application number PCT/GB2003/002345, incorporated herein by reference. However, in accordance with the present invention the surfaces of the microelectrodes are preferably modified or functionalised so as to be particularly sensitive to certain species or chemical properties. The modification can be achieved either by monolayer coverage or by polymer layers up to micrometer thickness.

Surface modifications of the boron-doped diamond microelectrodes can be performed by one of several different means. Metal oxide nanoparticles can be adsorbed onto the boron-doped diamond microelectrodes, as for example described by McKenzie et al. (Electrochemistry Communications, volume 4, page 820, 2002). Further derivatisation of the metal oxide particles can be achieved, such as complexation with carboxylate- or thiol-containing ligands. Alternatively, metals may be deposited onto the surface of the microelectrodes using one of a variety of techniques, such as low-temperature plasma or direct metal evaporation/condensation. For example, Pitter et al. (Applied Physics Letters, volume 69, page 4035, 1996) used a direct evaporation/condensation technique to deposit silver metal onto boron-doped diamond; the silver metal deposited at ambient temperature formed small islands on the electrode surface. The metal or metal oxide deposit on the surface of boron-doped diamond microelectrodes can be used to further modify the electrode surface. For example, alkyl thiols, such as 1-octanethiol, can be used to generate hydrophobic surfaces by the formation of metal-sulphur bonds. Alternatively, hydrophilic surfaces can be generated using thiol-terminated carboxylic acids or amines, such as mercaptoacetic acid or a 4-mercaptopyridine; these derivations enable the surface to be either negatively or positively charged.

The surface of the boron-doped diamond microelectrodes can be directly functionalised by introducing oxygen to terminate the surface carbon atoms. For example, Nagao et al. (Japanese J. Applied Physics. Part 2. Letters, volume 36, page L1250, 1997) described the generation of oxygen-terminated boron-doped diamond films by boiling the film in chromic acid and aqua regia (a mixture of nitric and hydrochloric acids). The oxygen terminals of the boron-doped diamond can be used to graft a variety of functional groups onto the electrode surface. For example, the surface can be made hydrophobic by reaction with chlorodimethyloctylsilane, which generates a C—O—Si— linkage to graft the hydrophobe onto the electrode surface. Similarly, other functionalisations are possible to graft ionophores and other redox centres onto the surface.

According to one preferred embodiment the diamond working electrode surfaces are modified using N,N'-dimethylphenylenediamine (DMPD), or a structural analogue, together with a conducting sphere of micrometer scale (carbon or boron carbide), or nanometer scale (carbon nanotubes, or metal nanoparticles). These species can be spikes together with a thin layer of microporous epoxy with certain ratio, thus leads to a all-solid state, functionalised electrode surface that is sensitive to the concentration of hydrogen sulfide. See, co-pending GB Patent Application number 0217249.2, filed 25 Jul. 2002, incorporated herein by reference.

According to another preferred embodiment, the diamond microelectrodes are used to measure pH by modifying the working electrode surfaces through the reduction of aryl diazonium salts. For example, see Kuo et al. (*Electrochem. & Solid-State Lett.*, volume 2, page 288, 1999). Derivatives of anthraquinone can be grafted onto the boron-doped diamond electrode to yield a pH electrode, as for example achieved by Ojani et al. on carbon paste electrodes (*Iran. J. Chem. & Chem. Eng.*, volume 20, page 75, 2001) using the physical mixing of anthraquinone derivatives with carbon paste. Downard (*Electroanalysis*, volume 12, page 1085, 2000) has described a large number of modified carbon electrodes generated by the reduction of aryl diazonium salts.

According to another preferred embodiment, the diamond based sensor is used to sense non-chemical fluid properties such as resistivity. In particular, the diamond microelectrodes can be used to measure the redox behaviour and conductivity of highly resistive liquids, such as oils and lubricants. For example, Kauffman (U.S. Pat. No. 5,071,527) has described a three electrode arrangement of working, reference and counter microelectrodes that are capable of performing cyclic voltammetry and conductivity measurements on oil and lubricant samples to determine their remaining useful life, such determination of the depletion of antioxidants. Kauffman specified that the preferred materials for the microelectrodes described in the patent were platinum and gold, but the use of boron-doped diamond microelectrodes could be advantageous, e.g., low reactivity with the polar compounds found in oils and lubricants, such as sulphur-containing compounds, anti-wear additives and boundary lubricants.

FIGS. 5a and 5b show the placement of a diamond based microelectrode array in a housing, according to a preferred embodiment of the invention. Microelectrode array 100 is preferably as described in FIGS. 1a and 1b, but may also be as elsewhere described herein including in association with FIGS. 1c, 1d and 2-4. As shown in FIG. 5a, microelectrode array 100 is assembled into an electrochemical device 180, in which the diamond based microelectrodes are used as the working electrode. Device 180 also preferably comprises a counter electrode 204 (preferably made of platinum) and a reference electrode 206 (preferably made of Ag\AgCl or Ag\AgI or a short piece of platinum as pseudo-reference). The microelectrode array 100 is constructed on top of a substrate 202 which is preferably made of polyetheretherketone (PEEK) material.

FIG. 5b shows a perspective view of electrochemical device 180. In this embodiment, electrodes 210, 212 and 214 are electrically connected to, respectively, the counter electrode 204, reference electrode 206 and working electrode, which consists of microelectrodes 100 as shown in FIG. 5a.

FIG. 6 is an electrical schematic diagram showing a preferred circuit layout for an electrochemical sensor, according to the invention. The electrical connections 210, 212 and 214 to, respectively, the counter electrode, reference electrode and working electrode are shown. Using a circuit as shown in FIG. 6, the output signal can be used to indicate the particular species and/or chemical properties according to the type of microelectrode array being used. The electronics shown in FIG. 6 can be obtained commercially from vendors such as Alphasense Limited (www.alphasense.com).

Figure 7:
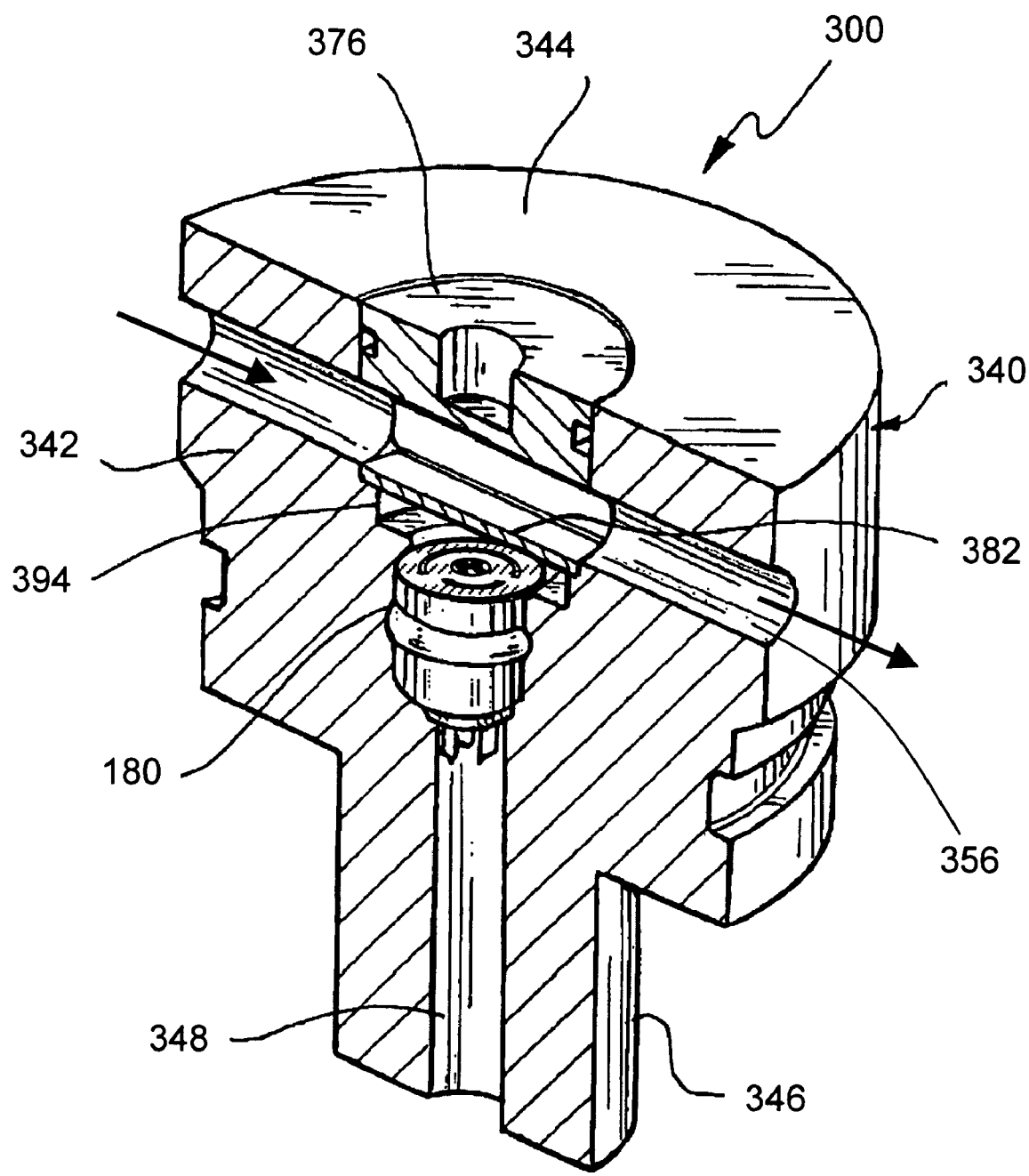
FIG. 7 shows a sensor based on a microelectrode array according to a preferred embodiment of the invention.

FIG. 7 shows an electrochemical sensor based on a microelectrode array according to a preferred embodiment of the invention. The sensor 300 comprises a generally cylindrical housing 340, which is preferably made from PEEK and which comprises a main housing member 342 having an upper portion 344, a reduced diameter lower portion 346, and a stepped diameter cylindrical bore 348 extending coaxially through it from top to bottom. The bore 348 has a large diameter upper portion wholly within the upper portion 344 of the main housing member 342, an intermediate diameter portion also wholly within the upper portion of the main housing member, and a reduced diameter portion largely within the lower portion 346 of the main housing member.

A flowpath 356 for the fluid to be sensed extends diametrically through the upper portion 344 of the main housing member 342, intersecting the upper portion 350 of the bore 348.

Disposed in the intermediate diameter portion of the bore 348, and resting on the shoulder defined between the reduced diameter portion and the intermediate diameter portion, is a cylindrical electrochemical device 180 as described more fully above. An O-ring made of VITON™ is disposed in a groove extending coaxially round the body of device 180 to seal the device within the intermediate diameter portion of the bore 348.

Disposed in the large diameter upper portion of the bore 348, and resting on the shoulder defined between the intermediate diameter portion and the large diameter portion is a cylindrical membrane retainer assembly 376, which comprises a cup-shaped housing member, a cylindrical housing member which screws part of the way into the cup-shaped housing member, and a gas permeable membrane 382 preferably in the form of a circular plate made of zeolite or other suitable ceramic material coaxially located in the cup-shaped housing member, in the space between the bottom of the inside of the cup shape of the housing member and the bottom of the cylindrical housing member. The cylindrical housing member has a diametrically extending flow path therethrough being aligned with the flow path 356 in the upper part 344 of the main housing member 342.

According to a preferred embodiment, sensor 300 is adapted to sense hydrogen sulphide. According to this embodiment, the generally cylindrical space 394 beneath the underside of the membrane 382 and the top of the device 180 constitutes a reaction chamber, and is filled with a reaction solution containing a precursor or catalyst, for example, dimethylphenylenediamine (DMPD).

According to other embodiments, membrane 382 is not provided. In many applications it is better not to use a membrane, since mass transfer is faster and direct contact between the microelctrodes and the fluid allow for greater accuracy in measurement of concentration or chemical property. An example of where a membrane is not preferred is sensing pH in a single phase aqueous solution. However, in some cases a membrane is preferred, for example if the fluid being monitored includes a non-aqueous solvent which may impair electrical connectivity to the electrodes, or in extreme cases the fluid may result in fouling of the modified surface.

Figure 8:
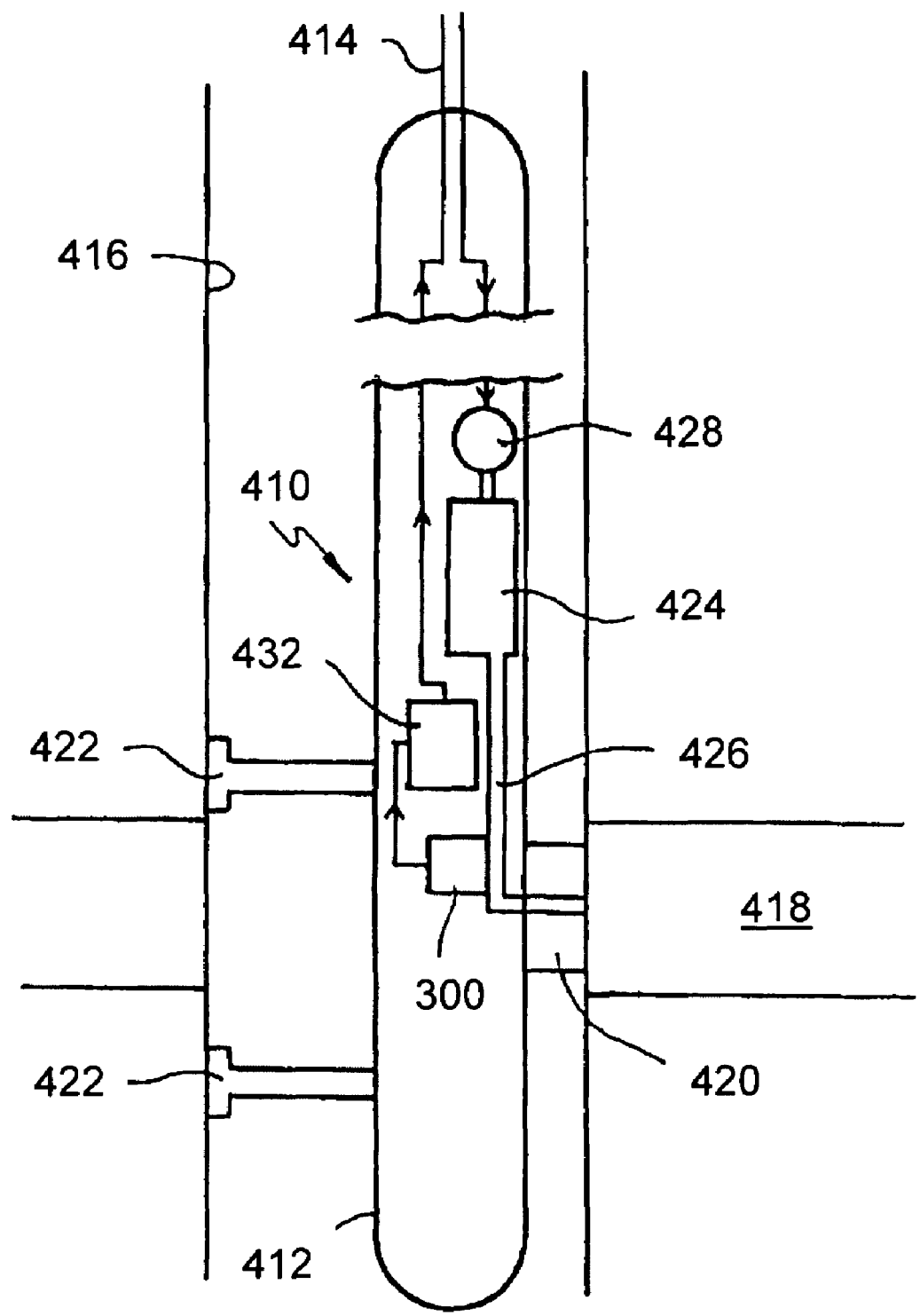
FIG. 8 is a schematic representation of a wellbore tool which is positioned in a wellbore and which is equipped with a sensor in accordance with the present invention.

FIG. 8 is a schematic representation of a wellbore tool which is positioned in a wellbore and which is equipped with an electrochemical sensor in accordance with the present invention. The wellbore tool shown in FIG. 8 is indicated at 410, and is based on Schlumberger's modular dynamics tester (MDT), as described in Trans. SPWLA 34$^{th}$ Annual Logging Symposium, Calgary, June 1993, Paper ZZ and in U.S. Pat. Nos. 3,780,575, 3,859,851, 4,994,671, co-pending PCT patent application number PCT/GB2003/002345 and co-pending GB Patent Application number 0217249.2, all incorporated herein by reference. The tool 410 comprises an elongated substantially cylindrical body 412, which is suspended on a wireline 414 in the wellbore, indicated at 416, adjacent an earth formation 418 believed to contain recoverable hydrocarbons, and which is provided with a radially projecting sampling probe 420. The sampling probe 420 is placed into firm contact with the formation 418 by hydraulically operated rams 422 projecting radially from the body 412 on the opposite side from the sampling probe, and is connected internally of the body to a sample chamber 424 by a conduit 426.

In use, and prior to completion of the well constituted by the wellbore 416, a pump 428 within the body 412 of the tool 410 can be used to draw a sample of the hydrocarbons into the sample chamber 424 via the conduit 426. The pump is controlled from the surface at the top of the wellbore via the wireline 414 and control circuitry (not shown) within the body 412. It will be appreciated that this control circuitry also controls valves (not shown) for selectively routing the sampled hydrocarbons either to the sample chamber 424 or to a dump outlet (not shown), but these have been omitted for the sake of simplicity.

In accordance with the present invention, the conduit 426 additionally communicates with an electrochemical sensor 300 also provided within the body 412 of the tool 410, so that the hydrocarbons flow over a face of the sensor on their way through the conduit. The sampling probe is located close to the electrochemical sensor 300, at a distance comprised between 8 and 30 cm from said electrochemical sensor, advantageously approximately equal to 15 cm. The sensor 300 produces an output current, which is dependent on the amount of species or chemical property sensor 300 is adapted to detect in the hydrocarbons flowing through the conduit 426. This output current is measured in known manner by a digital current measuring circuit 432 (as described in connection with FIG. 6) in the body 412 of the tool 410, and the measurement is transmitted to the surface via the wireline 414.

Although FIG. 8 depicts an open hole sampling tool, it will be recognized that the present invention is also applicable for use with downhole sampling tools for cased hole as well. For example, according to one embodiment the sensor 300 is integrated for use with the Cased Hole Dynamics Tester (CHDT) tool from Schlumberger. See, e.g. the CHDT product brochure: http://www.hub.slb.com/Docs/connect/formation_evaluation/ Cased_Hole_Dynamics_Tester/graphics/CHDT.pdf, incorporated herein by reference.

Figure 9:
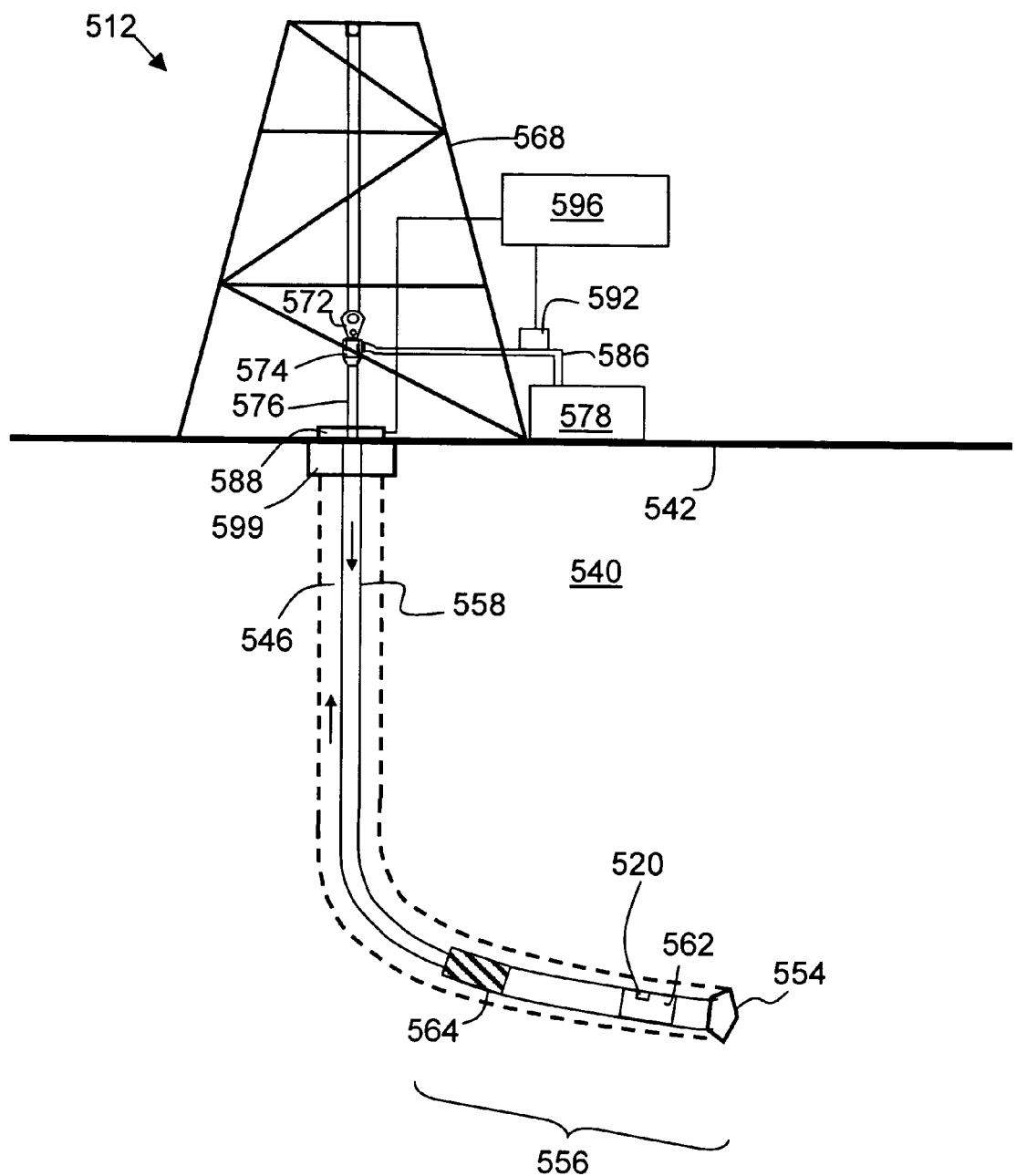
FIG. 9 shows a drilling system using a diamond-based sensor, according to a preferred embodiment of the invention.

FIG. 9 shows a drilling system using a diamond-based sensor, according to a preferred embodiment of the invention. Drill string 558 is shown within borehole 546. Borehole 546 is located in the earth 540 having a surface 542. Borehole 546 is being cut by the action of drill bit 554. Drill bit 554 is disposed at the far end of the bottom hole assembly 556 that is attached to and forms the lower portion of drill string 558. Bottom hole assembly 556 contains a number of devices including various subassemblies. According to the invention measurement-while-drilling (MWD) subassemblies are included in sensor subassembly 562. According to the invention a subassembly 562 is provided to make measurements using a diamond based sensor as herein described. The signals from the sensor subassembly 562 are preferably communicated to pulser assembly 564. Pulser assembly 564 converts the information from subassembly 562 and other subassemblies into pressure pulses in the drilling fluid. The pressure pulses are generated in a particular pattern which represents the data from the subassemblies. The pressure pulses travel upwards though the drilling fluid in the central opening in the drill string and towards the surface system.

The drilling rig 512 includes a derrick 568 and hoisting system, a rotating system, and a mud circulation system. The hoisting system which suspends the drill string 558, includes traveling block and hook 572 and swivel 574. The rotating system includes kelly 576, rotary table 588, and engines (not shown). The rotating system imparts a rotational force on the drill string 558 as is well known in the art. Although a system with a Kelly and rotary table is shown in FIG. 9, those of skill in the art will recognize that the present invention is also applicable to top drive drilling arrangements. Although the drilling system is shown in FIG. 9 as being on land, those of skill in the art will recognize that the present invention is equally applicable to marine environments.

The mud circulation system pumps drilling fluid down the central opening in the drill string. The drilling fluid is often called mud, and it is typically a mixture of water or diesel fuel, special clays, and other chemicals. The drilling mud is stored in mud pit 578. The drilling mud is drawn in to mud pumps (not shown), which pumps the mud though stand pipe 586 and into the kelly 576 through swivel 574 which contains a rotating seal. In invention is also applicable to underbalanced drilling. If drilling underbalanced, at some point prior to entering the drill string, gas is introduced into drilling mud using an injection system (not shown).

The mud passes through drill string 558 and through drill bit 554. As the teeth of the drill bit grind and gouges the earth formation into cuttings the mud is ejected out of openings or nozzles in the bit with great speed and pressure. These jets of mud lift the cuttings off the bottom of the hole and away from the bit, and up towards the surface in the annular space between drill string 558 and the wall of borehole 546.

According to the invention, a diamond-based sensor 520 is mounted on sensor subassembly 562. If fluid to be monitored is the wellbore fluid passing upwards to the surface, the sensor 520 is mounted on or near the outer surface of the subassembly so as to be exposed to wellbore fluids passing upwards toward the surface. For example, according to one embodiment, sensor 520 is adapted to sense hydrogen sulfide as herein described.

At the surface the mud and cuttings leave the well through a side outlet in blowout preventer 599 and through mud return line (not shown). Blowout preventer 599 comprises a pressure control device and a rotary seal. The mud return line feeds the mud into separator (not shown) which separates the mud from the cuttings. From the separator, the mud is returned to mud pit 578 for storage and re-use. Mud pulses traveling up the drillstring are detected by pressure sensor 592. Pressure sensor 592 comprises a transducer that converts the mud pressure into electronic signals. The pressure sensor 592 is connected to surface processor 596 that converts the signal from the pressure signal into digital form, stores and demodulates the digital signal into useable MWD data.

Figure 10:
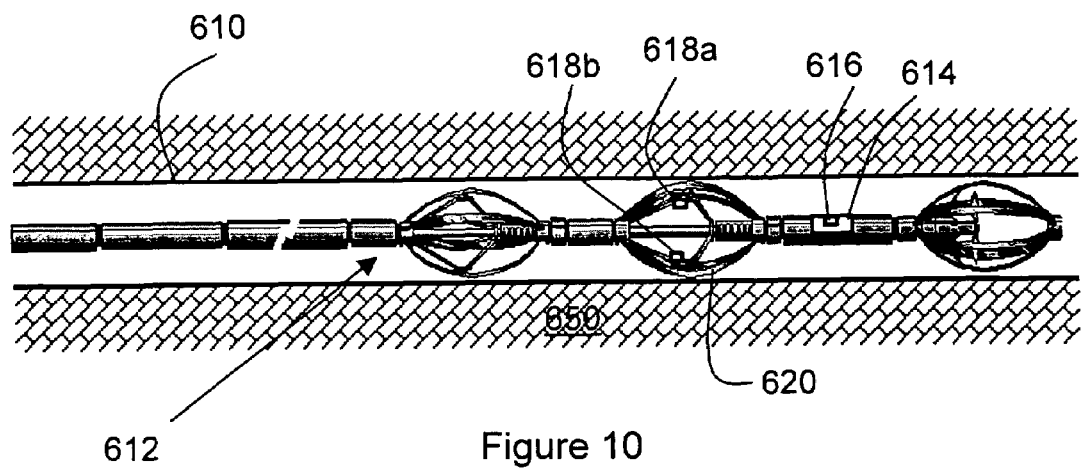
FIG. 10 shows a diamond based sensor incorporated into a production logging tool to monitor fluid in a horizontal section of a well.

FIG. 10 shows a diamond based sensor incorporated into a production logging tool to monitor fluid in a horizontal section of a well. Production logging tool 612 is shown positioned on a wireline within horizontal section 610 of a well in formation 650. The horizontal section 610 may be either cased or open hole. The production logging tool includes a number of separate sensors for taking independent measurements such as total flow rate, phase velocity, flow imaging, water flow, etc. Preferably a number of diamond based sensors are mounted near centralizer 620. As shown diamond based sensors 618a and 618b are mounted on separate members just inside different arms of centralizer 620. Mounting the sensors in this advantageously allows for different parts of the flow to be monitored, such as would be useful when the flow in the well is stratified. In cases where the flow is not stratified, or the separate measurements of the different phases are not needed, a diamond bases sensor 616 is mounted on a subassembly 614 on the main body of the logging tool 612. According to one preferred embodiment the diamond bases sensors are adapted to sense hydrogen sulfide as is described herein.

Figure 11:
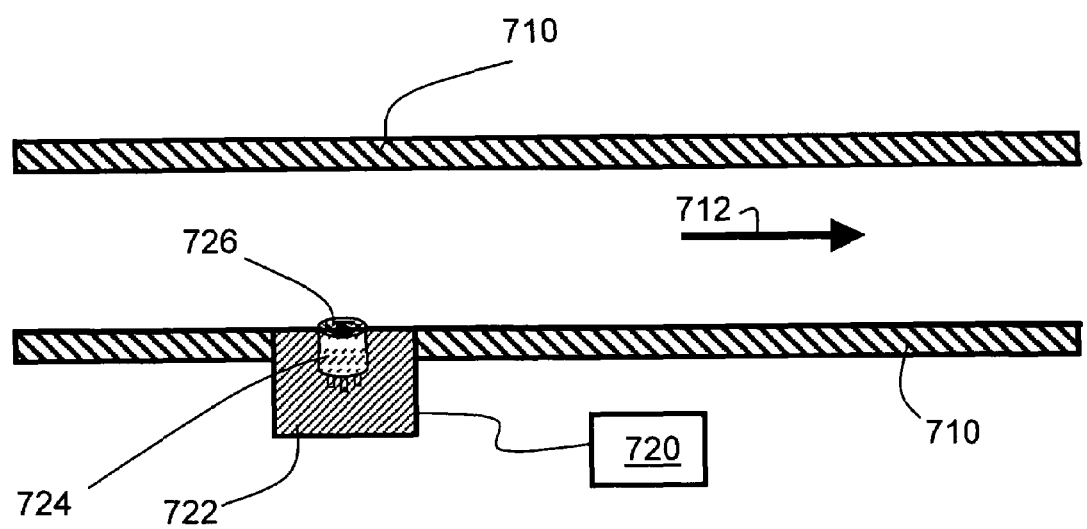
FIG. 11 shows a diamond based sensor used to monitor fluid flowing in a conduit, according to embodiments of the invention.

FIG. 11 shows a diamond based sensor used to monitor fluid flowing in a conduit, according to embodiments of the invention. The fluid to be monitored flows through conduit 710 in the direction indicated by arrow 712. Sensor housing 722 is provided to house sensor body 724 which includes a diamond-based micro electrode structure 726 as described herein. The electrical signals from the microelectrode structure is interpreted by processed 720 as described herein. According to preferred embodiments, conduit 710 carries wellbore fluid and is placed either downhole or on the surface of an oil well. The sensor is used to sense fluid properties such as resistivity or pH, or particular chemical species such as hydrogen sulphide as herein described.

According to another embodiment conduit 710 is part of a chemical processing facility and sensor 724 is adapted to sense fluid properties or chemical species relevant to a chemical processing application. For example, using the functionalized surface modifications of the microelectrode surfaces as describe herein, the diamond based sensor can be used to sense various chemical species, chemical properties such as pH, and other characteristics of the fluid in conduit 710 such as resistivity. According to another embodiment, the sensor 724 is used for environmental monitoring.

According to another embodiment, conduit 710 is used for CO2 sequestration using wellbores and sensor 724 is used for monitoring pH as is described herein.

According to another embodiment, sensor 724 is used to monitor hydrogen sulphide when monitoring volcanic activity.

While the invention has been described in conjunction with the exemplary embodiments described above, many equivalent modifications and variations will be apparent to those skilled in the art when given this disclosure. Accordingly, the exemplary embodiments of the invention set forth above are considered to be illustrative and not limiting. Various changes to the described embodiments may be made without departing from the spirit and scope of the invention.

What is claimed is:

1. A sensor for monitoring one or more characteristics associated with a fluid, comprising:
   a housing;
   an insulating layer comprising non-conducting diamond positioned within said housing and having a surface exposed directly or indirectly to the fluid;
   a plurality of microelectrodes each comprising electrically conducting diamond and having a surface exposed directly or indirectly to the fluid, wherein a thickness of each of the microelectrodes is greater than 1 mm; and
   an electrical circuit in electrical communication with each of the microelectrodes adapted to convert electrical signals from the microelectrodes into at least one signal associated with a characteristic being monitored.

2. The sensor according to claim 1 wherein the size of the exposed surface of each microelectrode is less than 8000 sq. microns.

3. The sensor according to claim 2 wherein the size of the exposed surface of each microelectrode is less than 2000 sq. microns.

4. The sensor according to claim 3 wherein the size of the exposed surface of each microelectrode is less than 500 sq. microns.

5. The sensor according to claim 4 comprising at least seven microelectrodes.

6. The sensor according to claim 5 comprising at least 19 microelectrodes.

7. The sensor according to claim 6 comprising at least 50 microelectrodes.

8. The sensor according to claim 5 wherein the microelectrodes are arranged within the insulating layer such that the exposed surfaces of the microelectrodes form an irregular pattern.

9. The sensor according to claim 5 wherein a distance between two adjacent microelectrodes is at least five times the diameter of a circle having an area equal to an area of an exposed surface of each microelectrode.

10. The sensor according to claim 9 wherein the distance between two adjacent microelectrodes is at least ten times the diameter of a circle having an area equal to the area of the exposed surface of each microelectrode.

11. The sensor according to claim 4 wherein the microelectrodes are arranged within the insulating layer such that the exposed surfaces of the microelectrodes form a regular pattern.

12. The sensor according to claim 11 wherein said pattern is a hexagonal pattern.

13. The sensor according to claim 12 wherein said pattern is a square pattern.

14. The sensor according to claim 1 where the microelectrodes are positioned within the insulating layer and the exposed surface of each of the microelectrodes is co-planar with the exposed surface of the insulating layer.

15. The sensor according to claim 1 further comprising a counter electrode mounted within the housing and having a surface exposed directly or indirectly to the fluid, and wherein the microelectrodes form a working electrode.

16. The sensor according to claim 15 further comprising a reference electrode mounted within the housing and having a surface exposed directly or indirectly to the fluid flowing in the flow channel.

17. The sensor according to claim 15 further comprising a gas permeable membrane mounted between the fluid and the exposed surfaces of the insulating layer and the microelectrodes, wherein the sensor is adapted to sense characteristics associated with a gas that is allowed to pass though the membrane.

18. The sensor according to claim 1 wherein the housing is made from polyetheretherketone.

19. The sensor according to claim 1 wherein a characteristic associated with the fluid being monitored is a chemical property of the fluid.

20. The sensor according to claim 19 wherein the chemical property being monitored by the sensor is a pH of the fluid.

21. The sensor according to claim 20 wherein the exposed surface of each microelectrode is modified so as to be sensitive to pH.

22. The sensor according to claim 1 wherein a characteristic associated with the fluid being monitored is the presence of a chemical species within the fluid.

23. The sensor according to claim 22 wherein a characteristic associated with the fluid being monitored is the concentration of a chemical species within the fluid.

24. The sensor according to claim 22 wherein the chemical species is hydrogen sulphide.

25. The sensor according to claim 24 wherein the exposed surface of at least one of the microelectrodes is modified using N,N'-dimethyl-phenylenediamine, or a structural analogue.

26. The sensor according to claim 1 wherein a characteristic associated with the fluid being monitored is the resistivity of the fluid.

27. The sensor according to claim 26 wherein the fluid is a highly resistive liquid.

28. A wellbore sensor system for monitoring fluids produced from one or more wellbores comprising the sensor according to claim 1.

29. The wellbore sensor system according to claim 28 further comprising a wellbore fluids sampling tool, wherein the sensor is mounted within the sampling tool.

30. The wellbore sensor system according to claim 29 wherein the sampling tool is adapted to sample wellbore fluids in open hole sections of a wellbore.

31. The wellbore sensor system according to claim 29 wherein the sampling tool is adapted to sample wellbore fluids in cased hole sections of a wellbore.

32. The wellbore sensor system according to claim 29 further comprising a production logging tool, wherein the sensor is mounted on a portion of the production logging tool.

33. The wellbore sensor system according to claim 28 further comprising a subassembly for sensing characteristics within a wellbore during the drilling process, wherein the sensor is mounted with the subassembly which is adapted to be part of a bottom hole assembly.

34. The wellbore sensor system according to claim 28 wherein the one or more wellbores are drilled in a water reservoir.

35. The wellbore sensor system according to claim 28 wherein the one or more wellbores are used for CO2 sequestration, and the sensor is used to monitor pH.

36. The wellbore sensor system according to claim 28 wherein the sensor is coupled with a conduit through which the produced fluids flow.

\* \* \* \* \*